United States Patent [19]

Muz

[11] Patent Number: 5,094,240
[45] Date of Patent: Mar. 10, 1992

[54] PULSE/OXYGEN SENSOR AND METHOD OF MAKING

[75] Inventor: Edwin Muz, Reutlingen, Fed. Rep. of Germany

[73] Assignee: Nicolay GmbH, Kirchheim/Teck, Fed. Rep. of Germany

[21] Appl. No.: 324,454

[22] Filed: Mar. 16, 1989

[30] Foreign Application Priority Data

Mar. 18, 1988 [DE] Fed. Rep. of Germany ....... 3809084

[51] Int. Cl.⁵ .................. A61B 5/14; A61B 5/0245
[52] U.S. Cl. ................... 128/633; 128/687; 128/666
[58] Field of Search .............. 128/633, 634, 665, 666, 128/687

[56] References Cited

U.S. PATENT DOCUMENTS

| | | | |
|---|---|---|---|
| 4,685,464 | 8/1987 | Goldberger et al. | 128/633 |
| 4,723,554 | 2/1988 | Oman et al. | 128/666 |
| 4,825,872 | 5/1989 | Tan et al. | 128/633 |
| 4,825,879 | 5/1989 | Tan et al. | 128/633 |
| 4,830,014 | 5/1989 | Goodman et al. | 128/665 |
| 4,865,038 | 9/1989 | Rich et al. | 128/633 |

Primary Examiner—Kyle L. Howell
Assistant Examiner—John Hanley
Attorney, Agent, or Firm—Roylance, Abrams, Berdo & Goodman

[57] ABSTRACT

A sensor for the noninvasive measurement of the pulse rate and/or oxygen saturation of the blood of a person has a housing holding a transmitter and a receiver. The housing has thin, light-permeable layers in the areas of the light source surface of the transmitter and the light detecting surface of the receiver. Both the transmitter and the receiver are mounted on a flexible conductor plate. The housing is formed of a tight sheathing covering the transmitter, the receiver and the conductor plate supporting the transmitter and receiver.

11 Claims, 3 Drawing Sheets

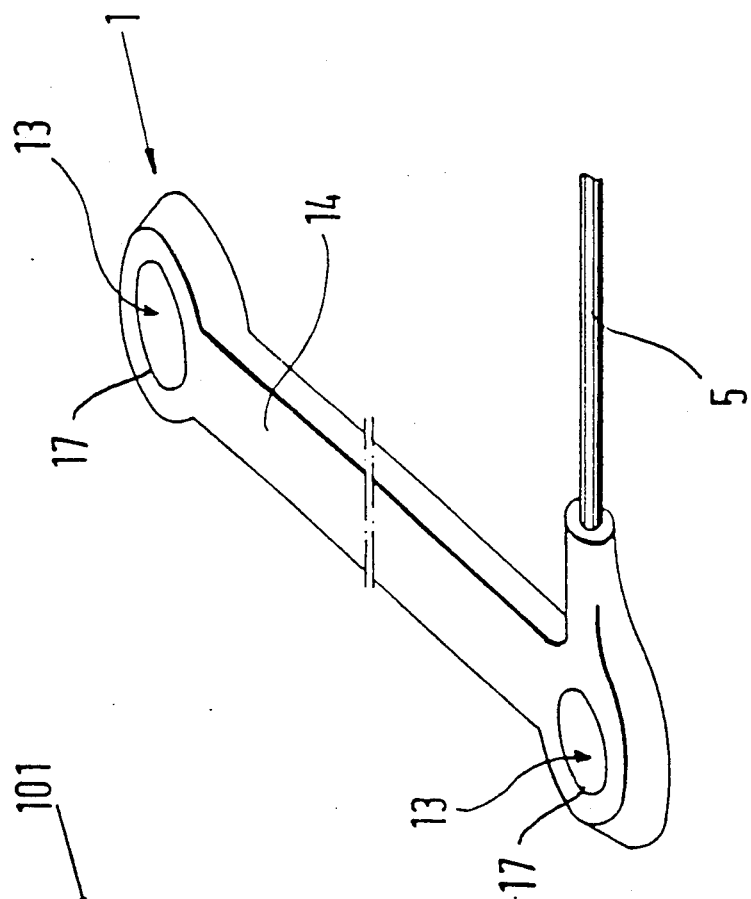
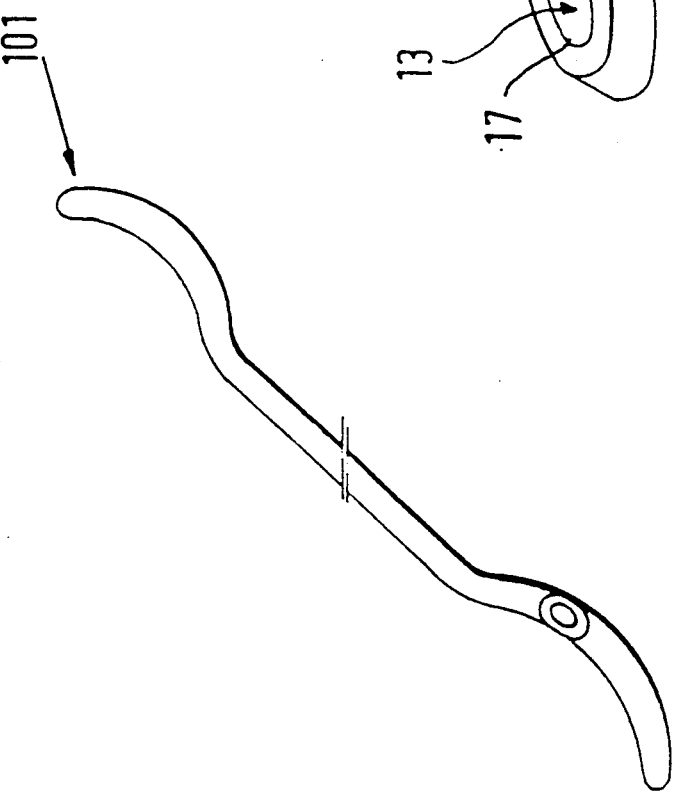

PULSE/OXYGEN SENSOR AND METHOD OF MAKING

FIELD OF THE INVENTION

The present invention relates to a sensor for noninvasive measurement of the pulse rate and/or the oxygen saturation of the blood of a person, employing a light source transmitter and a receiver sensitive to light emitted from the transmitter. Additionally, the present invention relates to a process for the manufacture of the sensor.

BACKGROUND OF THE INVENTION

A known sensor of this type, disclosed in U.S. Pat. No. 4,685,464, is configured in the form of a clothes line clip. The end of a patient's finger can be inserted between the two jaws of the clip. A hollow housing is placed on each of the two jaws. The housings face and are turned toward each other to form a trough to receive the end of the finger. An indentation, in the bottom of this trough, receives the transmitter or, respectively, the receiver. A thin layer of a light permeable material closes the indentation from the outside and covers the transmitter or, respectively, the receiver, forming a light permeable window. The two hollow housings are made of a soft elastic material, for example, silicon rubber, forming pads to distribute the pressure of the device uniformly on the surface of the finger.

SUMMARY OF THE INVENTION

An object of the present invention is to provide a sensor for noninvasive measurement of a patient's pulse rate and/or blood oxygen saturation using a light source transmitter and a light sensitive receiver which can be easily applied to the end of a patient's finger and anywhere else on the patient's body where a measurement is necessary.

Another object of the present invention is to provide a sensor for noninvasive measurement of a patient's pulse rate and/or blood oxygen saturation using a light source transmitter and a light sensitive receiver which can be applied for a relatively long time at the measurement site, without disturbing the patient.

A further object of the present invention is to provide a sensor for noninvasive measurement of a patient's pulse rate and/or blood oxygen saturation using a light source transmitter and a light sensitive receiver which is simple and inexpensive to manufacture and which is of rugged construction.

Yet another object of the present invention is to provide a process of making a sensor for noninvasive measurement of a patient's pulse rate and/or blood oxygen saturation, using a light source transmitter and a light sensitive receiver, which is simple to operate.

The foregoing objects are obtained by a sensor for noninvasive measurement of at least one of a patient's pulse rate and blood constituents. The sensor comprises a first flexible conductor plate, a light source transmitter and a receiver. The light source transmitter is enclosed in a transmitter housing and is mounted on the flexible conductor. The transmitter housing has a thin, light-permeable layer adjacent a light source of the transmitter. The receiver is sensitive to receiving light emitted from the transmitter, is enclosed in a receiver housing having a thin light-permeable layer adjacent a light detecting surface of the receiver, and is mounted on the flexible conductor. A tight sheathing forms the housing and encloses the conductor plate.

The sensor according to the present invention is protected with utmost security by the sheathing which prevents the infiltration of body fluids. Simple cleaning is guaranteed because of the sheathing and the flat shape of the sensor. The arrangement of the transmitter and the receiver on a flexible conductor plate leads to very small dimensions of the device and a flat shape. In addition, this sensor is lightweight and easily adaptable in its shape to the surface on which it must be placed for a measurement.

A higher level of insulation and a high electrical resistance potential of the electrically conductive paths of the sensor relative to the skin surface can be attained without any problem by virtue of the sheathing. Furthermore, the flat shape of the sensor according to the present invention, with its good adaptability to the skin surface at the test site, allows the sensor to adhere without problem to the skin surface or can be affixed to the skin surface by a clamp or holder. Finally, additional flexible conductive plates can provide a simple shielding barrier against stray electric effects.

The foregoing objects are also obtained by a process for making a sensor for noninvasive measurement of at least one of a patient's pulse rate and blood constituents having a light source transmitter and a receiver sensitive to light emitted from the transmitter, comprising the steps of mounting the transmitter and the receiver on a prefabricated support to form a structural unit of the support, receiver and transmitter, attaching a cable to the support, covering, at least partially, the structural unit by insulating members, and casting a light-impermeable, elastic material at least partially about the structural unit, ends of the cable attached to the structural unit and the insulating members.

Other objects, advantages and salient features of the present invention will become apparent from the following detailed description, which, taken in conjunction with the annexed drawings, discloses preferred embodiments of the present invention.

BRIEF DESCRIPTION OF THE DRAWINGS

Referring to the drawings which form a part of this disclosure:

FIG. 3 is a perspective view of the sensor of the first embodiment in its finished state after casting; and FIG. 4 is a side elevational view of a sensor according to a second embodiment of the present invention.

DETAILED DESCRIPTION OF PREFERRED EMBODIMENT

Figure 1:
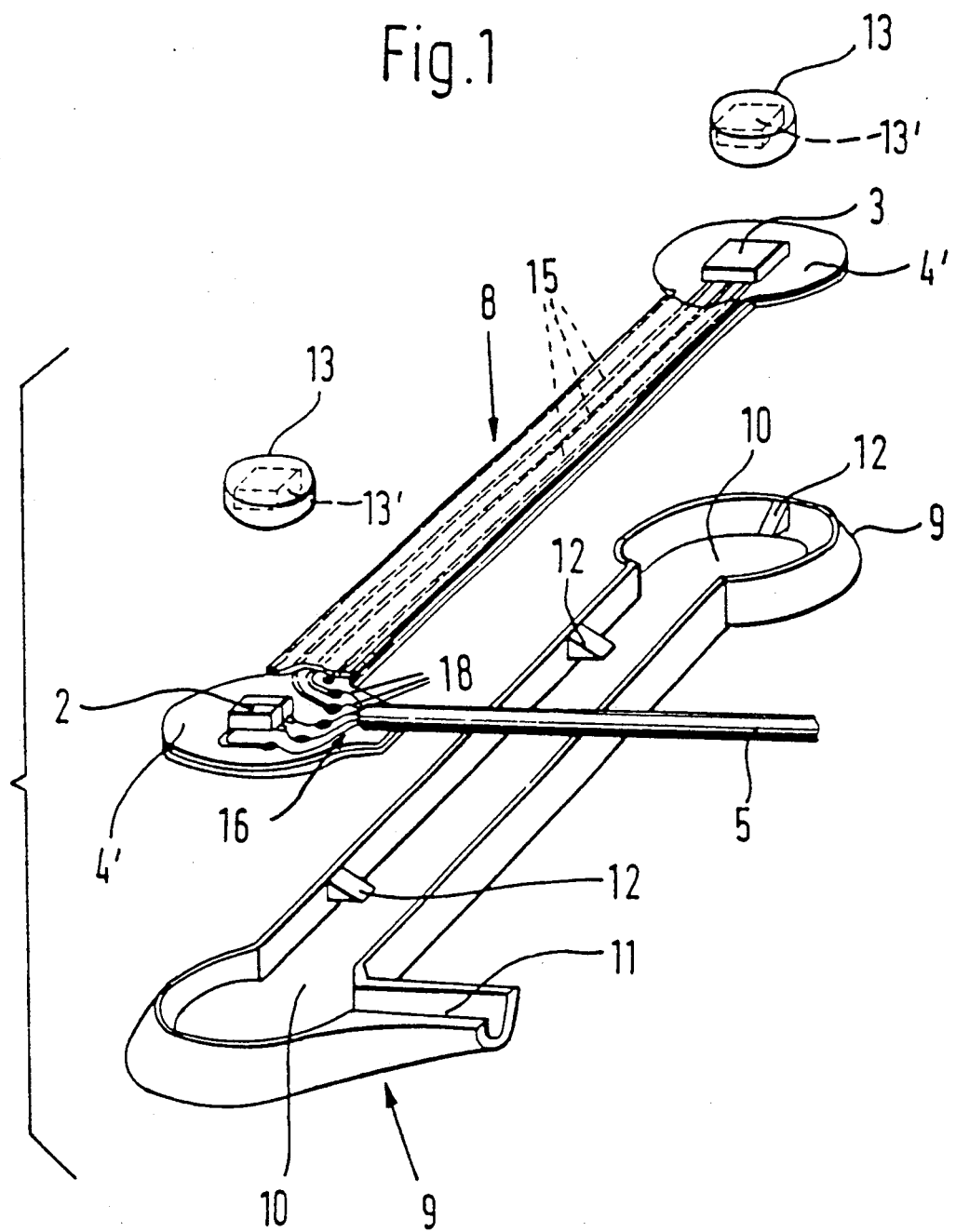
FIG. 1 is an exploded perspective view of individual parts of a sensor according to a first embodiment of the present invention before casting.

An optical electronic sensor 1 for noninvasive measurement of the pulse rate and/or oxygen saturation of a sample for testing, according to the present invention, uses of an optical beam acting upon the tissue of the sample. The sensor comprises a flexible conductor plate 4 serving as a support for a transmitter 2 and a receiver 3. In the exemplary embodiment, the transmitter is a light or radiation source comprising one or more light diodes. The receiver 3 comprises one or more phototransistors or photodiodes.

Conductor plate 4 comprises circular end segments 4' joined at opposite ends of a rod-like middle segment 4", and conductor paths 15 for transmitter 2 and receiver 3. The required conductor paths between end segments 4' extend longitudinally through middle segment 4". Transmitter 2 and receiver 3 are connected to the core leads 16 of distribution cable 5 by the conductor paths, which leads and paths are soldered together at the associated attachment points 18.

Conductor plate 4 forms the middle layer of a multilayer printed circuit 8. A first additional conductive plate 6 is laminated on the bottom of conductor plate 4.

The outside contour of conductive plate 6 corresponds to that of conductor plate 4. This first additional conductive plate 6 includes a copper layer 6' attached to an insulating layer 6" so as to form an electrical shield. Onto the top of conductor plate 4 supporting the conductor paths, a second additional conductive plate 7 is laminated. Conductive plate 7 covers only middle segment 4". This second additional conductive plate 7 also includes a copper layer 7' attached to an insulating layer 7 to form an electrical shield. This shield extends over almost the entire plate, as on the first additional conductive plate 6, with the exception of an edge area required for the connection, and the insulating layers 6" and 7" are interposed between the copper layers 6' and 7' and the conductor plate 6. The two additional conductive plates 6 and 7 are flexible, so that the entire multilayer printed circuit 8 is very flexible.

A lamellar, plate-shaped, flexible insulation member 9 of a light-impermeable material, as shown in FIG. 1, has an indentation 10. The boundary of insulation member 9 corresponds to or is fitted to the periphery of the printed circuit 8. A trough 11 is connected with indentation 10 to receive cable 5. The outside contour of insulation member 9 is somewhat larger than the contour of indentation 10 and trough 11, but is geometrically similar.

Instead of the oblique outside walls in the areas including end segments 4', as shown in FIG. 1, vertical upright side walls could also be provided, as is the case in the middle segment, and vice versa. As shown in FIG. 1, on the inside wall surface defining indentation 10, elastically ductile protrusions 12 are formed at some distance from the base of indentation 10. The protrusions extend into the indentation in such a manner as to catch the edge of printed circuit 8 and hold it tightly in the indentation, when printed circuit 8 is pressed into indentation 10.

Two cylindrical, identically constructed insulation bodies 13 are mounted over transmitter 2 and receiver 3. Bodies 13 are of a clear, and thus light-permeable material. Each body 13 has an indentation 13' in one surface adapted in shape and depth to the shape and height of transmitter 2 and receiver 3. The areas of the bodies turned away from or opposite to printed circuit 8 and aligned with indentations 13' in the two insulation bodies 13 have very thin walls and form optical windows for passage of the light beams or radiation in as unhindered a manner as possible. The electric insulation is nonetheless guaranteed to be unrestricted.

After printed circuit 8 is inserted into indentation 10 of preformed insulation member 9 and the end of cable 5 attached to the printed circuit is placed in trough 11, and after insulation bodies 13 are mounted on transmitter 2 and receiver 3, the structural unit thus formed is introduced into a plastic injection mold. In the mold, the structural unit is cast with a flexible, light impermeable plastic, for instance a heat-reticulating, two-component rubber material, in such a manner that the optical windows 17 of insulating bodies 13 remain free or exposed as illustrated in FIG. 3. The sheathing 14 formed by the casting process is combined tightly with insulating member 9 and with insulating bodies 13, whereupon the insulating member and bodies are combined tightly with one another to form an inside housing. Protrusions 12 hold printed circuit 8 tightly in the provided position during the casting process.

The sheathing can be quite thin where it engages on the outside of insulating member 9. It is even possible to configure sheathing 14 in a manner that it frees or exposes the bottom and the outside of insulating member 9, such that the sheathing is attached only to the surface defining the indentation 10. Thus, a sort of cover is formed for insulating member 9 covering printed circuit 8 and the end segment of cable 5 attached thereto, and is attached tightly to both insulating bodies 13.

Figure 2:
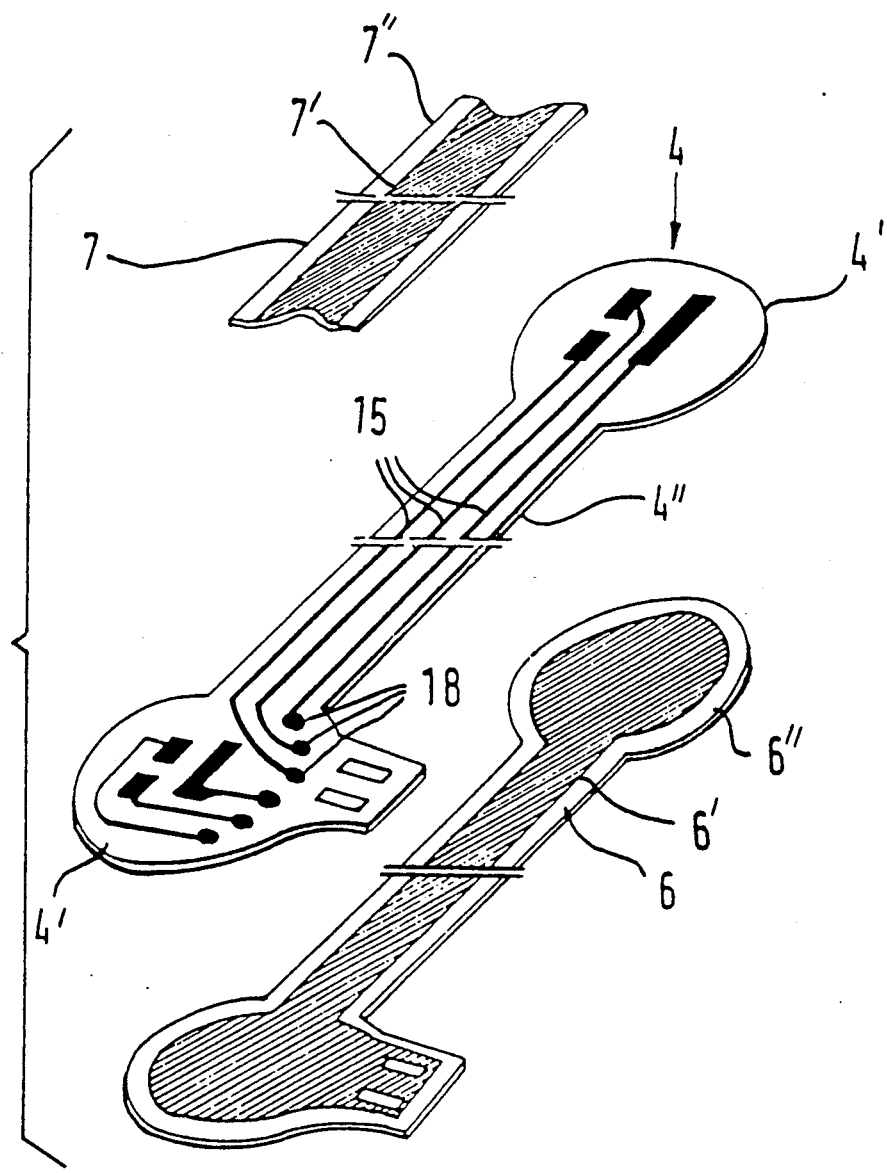
FIG. 2 is an exploded perspective view of the conductor plates of the sensor of the first embodiment.

The second exemplary embodiment, shown in FIG. 4, differs from the first exemplary embodiment of FIGS. 1 to 3 only in that sensor 101 has a preformed contact surface in each of the end segments containing the transmitter and the receiver. In the second embodiment the patient contact surface forms two troughs, which can be laid out matching or opposite one another to form a channel. Sensor 101, however, has a certain flexibility even in the area of these two troughs. In its middle segment, the flexibility of sensor 101 is exactly the same as that of sensor 1 of the first embodiment. The construction of sensor 101 and it manufacture do not differ from the embodiment of FIGS. 1 to 3.

While various embodiments have been chosen to illustrate the invention, it will be understood by those skilled in the art that various changes and modifications can be made therein without departing from the scope of the invention as defined in the appended claims.

What is claimed is:

1. A sensor for noninvasive measurement of at least one of a patent's pulse rate and blood constituents, comprising:

a conductor assembly having a flexible conductor plate;

a light source transmitter enclosed in a transmitter housing, said light source transmitter and said transmitter housing being fixedly mounted on said flexible conductor plate, said transmitter housing having a thin, light-permeable layer directly adjacent a light source of said transmitter;

a receiver sensitive to light emitted from said transmitter, said receiver being enclosed in a receiver housing having a thin light-permeable layer directly adjacent a light detecting surface of said receiver, said receiver and said receiver housing being fixedly mounted on said flexible conductor plate; and a sensor housing of a light-impermeable material enclosing said conductor plate and covering completely said conductor plate and partially covering said transmitter and receiver housings to define first and second optical windows at said thin light-permeable layers respectively, said sensor housing being attached tightly to said transmitter housing and said receiver housing for sealing said transmitter and receiver housings to said sensor housing to prevent infiltration of fluids therebetween;

whereby said optical windows remain directly exposed to the patient's skin.

2. A sensor according to claim 1, wherein said conductor assembly further includes a first electrically insulating layer mounted on a first side of said conductor plate and a first flexible conductive plate connected to said first insulating layer mounted on said conductor plate on said first side for shielding said conductor plate.

3. A sensor according to claim 2 wherein said conductor assembly further includes a second electrically insulating layer mounted on a second side of said conductor plate, opposite to said first side, and a second flexible conductive plate connected to said second insulating layer mounted on said conductor plate on said second side for shielding said conductor plate.

4. A sensor according to claim 1, wherein each of said transmitter and receiver housings is a performed cap with an indentation.

5. A sensor according to claim 3 wherein said sensor housing includes a flexible insulating member with said conductor plate, said transmitter and said receiver being receiver in an indentation of said flexible insulating member, and said sensor housing further includes a sheathing tightly closing said indentation.

6. A sensor according to claim 5 wherein said flexible insulating member of said sensor housing further comprises an extension having a channel for receiving a cable coupled to said first conductor plate.

7. A sensor according to claim 1 wherein said sensor housing has a contact surface portion formed into a predetermined shape.

8. A process for making a sensor for noninvasive measurement of least one of a patient's pulse rate and blood constituents having a light source transmitter and a receiver sensitive to light emitted from the transmitter, comprising the steps of:

fixedly mounting the transmitter and the receiver on a prefabricated conductor plate to form a structural unit of the plate, receiver and transmitter;

attaching a cable to the conductor plate so as to be electrically coupled to the transmitter and the receiver;

directly covering the transmitter and the receiver by light-permeable insulating members and mounting said insulating members on said conductor plate;

covering partially the structural unit by a preformed insulating member; and casting light-impermeable elastic material at least partially about the structural unit and an end of the cable attached to the structural unit to form together with the preformed insulating member a housing sealing the light-permeable insulating members to the light-impermeable elastic material to prevent infiltration of fluids therebetween and completely covering the structural unit and partially covering the light-permeable insulating members to define optical windows for the transmitter and the receive, whereby the optical windows remain directly exposed to the patient's skin.

9. A process according to claim 8 wherein the prefabricated conductor plate is flexible and connected to a conductive plate with an interposed insulating layer therebetween to form a multilayer printed circuit.

10. A process according to claim 8 wherein the prefabricated conductor plate is flexible and connected to two conductive plates with an interposed insulating layer between the conductor plate and each of the conductive plates such that the conductive plates function as shielding plates.

11. A process according to claim 8 wherein the elastic material used in the casting is a heat-reticulated, two-component rubber.

* * * * *